United States Patent [19]

Ouchi

[11] 4,407,273
[45] Oct. 4, 1983

[54] RAISING MEANS FOR GUIDING AN IMPLEMENT OF AN ENDOSCOPE

[75] Inventor: Teruo Ouchi, Kawagoe, Japan

[73] Assignee: Kabushiki Kaisha Medos Kenkyusho, Japan

[21] Appl. No.: 351,353

[22] Filed: Feb. 23, 1982

[30] Foreign Application Priority Data

Feb. 25, 1981 [JP] Japan .............................. 56-25595[U]
Oct. 13, 1981 [JP] Japan ........................... 56-152525[U]

[51] Int. Cl.³ .............................................. A61B 1/06
[52] U.S. Cl. ...................................................... 128/6
[58] Field of Search .................................. 128/4, 6–9, 128/307, 311, 328, 356

[56] References Cited

U.S. PATENT DOCUMENTS

| 3,897,775 | 8/1975 | Furihata | 128/6 |
| 3,903,877 | 9/1975 | Terada | 128/6 |
| 3,915,157 | 10/1975 | Mitsui | 128/6 |
| 4,190,041 | 2/1980 | Chikane | 128/6 |

Primary Examiner—Kyle L. Howell
Assistant Examiner—Max F. Hindenburg
Attorney, Agent, or Firm—Steinberg & Raskin

[57] ABSTRACT

In an endoscope having an optical fibre bundle for illumination communicating with an illumination window, an optical fibre bundle for observation communicating with a viewing window, an opening through which an implement, such as forceps for collection of vital tissue or tube for observation or photography of pancreatic duct or bile duct, is projected out, and a raiser adapted to bend the forward end of the implement to be guided into the visual field of the viewing window, wherein the opening is formed laterally of the viewing window and in parallel to the vertical plane including the optical central axis of the viewing window, and the raiser which is pivotally supported in the opening is adapted to be rotated in the vertical plane including the optical central axis of the viewing window and having a groove inclined towards the viewing window for guiding the implement into the visual field.

4 Claims, 19 Drawing Figures

RAISING MEANS FOR GUIDING AN IMPLEMENT OF AN ENDOSCOPE

BACKGROUND OF THE INVENTION (1) Field of the Invention

An endoscope having a viewing window for observation of the body cavity illuminated by light from an illumination window and wherein forceps for collecting vital tissue or a tube for introducing a contrast medium therethrough for photographing of the body organ are guided into the visual field of the viewing window.

(2) Description of Prior Art

It is known to provide raising means in an endoscope for raising and guiding the forward end of an implement, such as forceps for collecting a piece of vital tissue or a tube for introducing contrast medium therethrough for X-ray photography. The known raising means is provided with its working surface being inclined with respect to the vertical plane which includes the optical central axis of the viewing window to thereby guide the forward end of the implement into the visual field. However, the known raising means has various drawbacks due to the limited, narrow inner diameter of a channel through which the implement is introduced. The present invention is an improvement of such known raising means in the endoscope.

Thus, the present invention relates to raising means in endoscopes for implement such as forceps introduced to collect vital tissue of body cavity, for example, stomach or duodenum, or tubes introduced to observe or photograph pancreatic duct (ductus pancreaticus) or bile duct (tubulus biliferus), and more particularly to an improvement in raising means for, e.g., forceps introduced to collect vital tissue or tubes introduced to observe or photograph pancreatic duct or bile duct, such that, in diagnosis utilizing an endoscope inserted into a body cavity in question, said forceps or tube may be projected through an opening formed in a metal fitting at the front end of a flexible portion of the endoscope, the opening being situated in side-by-side relationship with a viewing window so that said forceps or tube thus projected may be appropriately guided into a visual field of said viewing window.

The endoscope generally includes, in its flexible tube to be inserted into the body cavity, two separate optical fibre bundles each comprising a bundle of fibre glass. One of these bundles is the optical fibre bundle for illumination adapted to emit light from the illuminating window formed adjacent the front end of the flexible tube to be inserted into the body cavity onto the inner wall of this body cavity to be inspected and this optical fibre bundle is connected at its opposite end, i.e., the end outside the body cavity with the light source for illumination. The other bundle is the optical fibre bundle for observation permitting the inner wall of the body cavity illuminated by the light emitted from said illuminating window to be viewed through said viewing window formed in the flexible tube adjacent its front end and through the manipulator unit adapted to be manipulated by the physician externally of the body cavity or to be photographed by the camera mounted in said manipulator unit. Briefly, one of these two optical fibre bundles is used to illuminate the interior of the body cavity and the other is used to observe the interior of the body cavity thus illuminated. Differing from such endoscopes which are exclusively used to observe or diagnose an inner wall of the body, particulary the diseased spot therein, there has recently been developed a multipurpose endoscope with the flexible tube to be inserted into the body cavity including the additional channel through which implements, such as forceps, can be introduced and externally manipulated to collect a part of the vital tissue for inspection, or through which a tube can be introduced to observe or photograph pancreatic duct or bile duct. The implement such as the forceps or the tube is introduced from the manipulator unit connected to the flexible tube at its end outside the body cavity through said channel extending through the flexible tube in parallel to said two optical fibre bundles into the body cavity in which said implement is projected outwardly from the flexible tube through its front end at a position adjacent the illuminating window and the viewing window towards the inner wall of the body cavity. The projected portion of the implement is selectively directed by external manipulation to the diseased spot to be inspected or to the pancreatic duct or the bile duct within the visual field of said viewing window. Obviously, said illuminating window and said viewing window are not formed in the end surface which extends in a plane orthogonal to the length of the flexible tube but in the peripheral outer wall of a substantially cylindrical metal fitting situated at the front end of said flexible tube for convenience of manipulation or diagnosis. It is obvious that the illuminating window is formed closely adjacent the viewing window, and said implement is projected orthogonally or transversely of the length of the flexible tube through the opening formed in the front end metal fitting adjacent the viewing window. To achieve this, the implement introduced along the channel axially extending through the flexible tube must abruptly change its direction at the position corresponding to said metal fitting around the front end of the flexible tube somewhat transversely of the direction in which the implement has been introduced. For such abrupt change of direction, said metal fitting is provided with a raising device or raising means adapted to raise the front end of the implement so that the direction in which said implement is projected may be freely controlled. The present invention relates to such raising means with which the metal fitting around the front end of the flexible tube is provided for controllably changing the direction in which the implement introduced into said flexible tube is projected. As will be apparent from the foregoing description, the illuminating window formed in the cylindrical outer wall of the metal fitting around the front end of the flexible tube should be able to adequately illuminate the visual field of the viewing window while the implement should be projected through the opening formed closely adjacent the viewing window so that the end of said implement thus projected out from said opening may be controllably oriented utilizing the visual field of the viewing window.

On the other hand, it is also required to arrange the raising means in close vicinity to said opening through which the end of the introduced implement is projected, and such that the raising means is adapted to be externally controlled from the manipulator unit connected to the outer end of the flexible tube by a wire connected to said manipulator unit, the wire extending through the flexible tube to the front end thereof, and associated with said raising means. Thus, various members must be crowded in the interior of the front end metal fitting and since the fitting has a relatively small diameter, the fitting necessarily has an extremely complicated inner construction. Specifically, this metal fitting must be provided with at least the illuminating window and the associated members, the viewing window and the associated members, a curved passage to guide the introduced implement and the raising means for this introduced implement. Additionally, the metal fitting must be incorporated therein with the air supply tube, the water supply and liquid suction tube to wash away mucus in the body cavity and the openings associated with these tubes. In consequence, it is difficult to provide sufficient space for these individual members. Particularly, for example, the front end metal fitting and the flexible tube following this metal fitting may be inserted through the oral cavity into the body cavity and therefore their outer diameters are necessarily governed by the minimum inner diameter of various organs in the body cavity. If the outer diameters of the front end metal fitting and the flexible tube are increased in order to facilitate incorporation of the respective members, there would be caused unbearable pain to the patient as said metal fitting and said flexible tube are advanced into the body cavity. On the other hand, if the outer diameters of said metal fitting and said flexible tube directly connected therewith are reduced in order to ease pain to the patient as effectively as possible and to facilitate insertion thereof into the body cavity, a technical difficulty in mounting the respective members within the front end metal fitting and the flexible tube would occur. The problem would be very serious particularly if the outer diameter of said optical fibre bundle for illumination is reduced, because the light quantity which is available to illuminate the diseased spot would be thereby limited. This would be similar in the case where the diameter of the optical fibre bundle for observation is reduced. Thus, if the outer diameter of said optical fibre bundle for observation is reduced, the visual field for observation would be so constricted or darkened that the desired operation of observation or photographing might be disadvantageously obstructed. As a result, it is impossible to reduce the outer diameters of these optical fibre bundles to the desired values.

SUMMARY OF THE INVENTION

A first object of the present invention is to enlarge as far as possible under the various restrictions as mentioned above the inner diameter of the channel necessary to guide the implement therethrough until the front end of this implement is projected outwardly through the associated opening formed in the metal fitting provided at the front end of the flexible tube while facilitating a reliable guidance of said front end of the implement projected through said opening into the visual field for observation.

A second object of the present invention is to design the overall arrangement and individual configurations of the respective members within the front end metal fitting of which provides an extremely limited space so that, in performing an inspection with said front end metal fitting and the part of the flexible tube immediately following said metal fitting inserted into the body cavity, vital tissue may be collected even from a part of the diseased organ which is defined by plaits or valves as relatively short sections in the direction of said insertion.

A third object of the present invention is to enlarge the inner diameter of the channel necessary to guide the implement therethrough while minimizing the force required for actuating raising means so that the latter may be easily remote-manipulated from the manipulator unit connected with the outer end of the flexible tube to achieve desired orientation or displacement of the implement and thereby to reduce a failure of manipulation.

A fourth object of the present invention is to enlarge the inner diameter of the channel necessary to guide the implement therethrough so that this channel may also serve to suck secretion or mucus from the body cavity.

Thus, the general object of the present invention is to provide an endoscope for vital tissue inspection having an improved operation by designing the overall arrangement and individual configurations of the respective members in an extremely limited cross-sectional area.

Briefly, in accordance with the present invention, these and other objects are attained by providing the front end metal fitting of the flexible tube of the endoscope with an opening from which the forward end of an implement, such as forceps for collection of vital tissue or a tube for observation or photography of pancreatic duct or bile duct, is projected, and wherein raising means are provided in the opening. The opening is situated laterally of the viewing window, the direction of the depth of the opening and a working surface of a raiser member of the raising means provided in the opening are positioned in parallel to the vertical plane including the optical central axis of the viewing window. The raiser member is provided with a groove which is slanted towards the viewing window for guiding the implement so that rotation of the raiser member, which is pivotally supported on a transverse axis crossing the vertical plane in the viewing window, causes the forward end of the implement to creep up along the slanted groove to be guided into the visual field of the viewing window.

Details of the raising device according to the present invention will be apparent to those skilled in the art from reading the following comparative description of front end metal fittings including associated raising means in the endoscope of the prior art and the endoscope according to the present invention both illustrated in the accompanying drawing.

DESCRIPTION OF THE DRAWING

FIG. 8A is a perspective view showing a raiser member incorporated within the front end metal fitting in the endoscope for vital tissue inspection of the prior art illustrated in FIGS. 5A and 6A;

FIG. 8B is a perspective view showing a raiser member incorporated within the front end metal fitting in the endoscope for vital tissue inspection according to the present invention;

FIG. 8C is a perspective view showing a raiser member incorporated within the front end metal fitting in the endoscope for vital tissue inspection according to the present invention;

DESCRIPTION OF PREFERRED EMBODIMENTS

Figure 1:
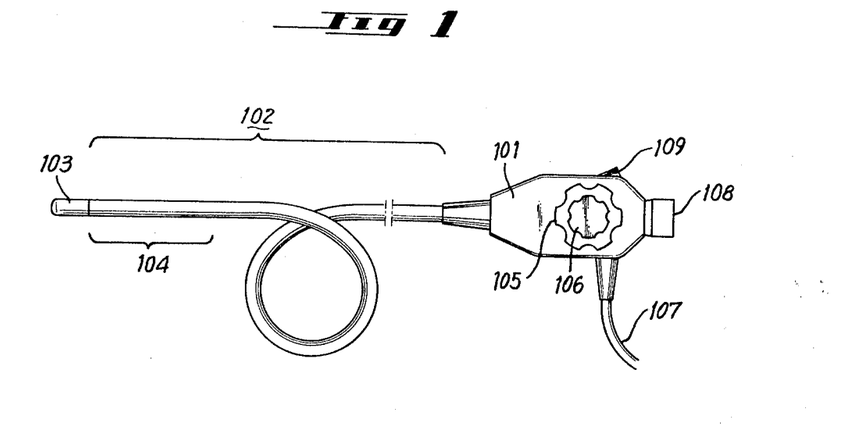
FIG. 1 is a schematic side view showing the external appearance of an endoscope for vital tissue inspection.

Referring to FIG. 1, reference numeral 101 designates a manipulator unit, 102 designates a flexible tube and 103 designates a front end metal fitting mounted on a front end of said flexible tube 102 so as to lead the insertion of said flexible tube 102 into a body cavity. A length 104 of the flexible tube 102 has a higher flexibility than the rest of length of the flexible tube 102 and is usually referred to as the bending portion thereof. The bending portion 104 can be bent right and left and up and down, as desired, by rotating two coaxial dials 105 and 106 provided on the manipulator unit 101 so as to direct the front end 103 towards a diseased spot in the same manner as in endoscopes of the prior art. Reference numeral 107 designates a tubular connector member which accommodates therein various members, such as an optical fibre bundle for illumination, an air supply tube, a water supply tube and a liquid suction tube and by which the optical fibre bundle for illumination is connected with a light source. Reference numeral 108 designates a viewer unit located at the external end of an optical fibre bundle for observation extending from the front end metal fitting 103 through the flexible tube 102 to the manipulator unit 101, and a photographic camera may be attached to this viewer unit as known in the art. Reference numeral 109 designates an inlet opening through which an implement 15, such as a cable provided with forceps or a tube for observation or photographing of body organs, such as the pancreatic duct or bile duct, is introduced into the body cavity.

Figure 2:
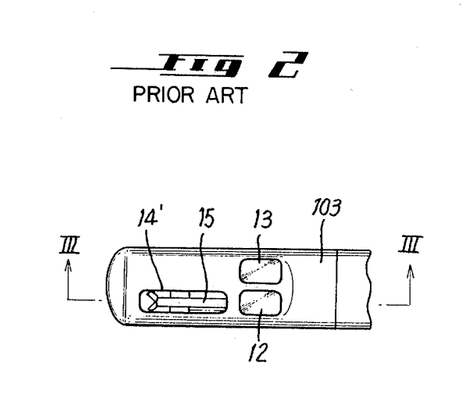
FIG. 2 is an enlarged plan view partially showing a front end metal fitting arranged at the front end of the flexible tube in an endoscope for vital tissue inspection of the prior art, in which a viewing window and an illuminating window are formed in lateral side-by-side relationship while an opening through which the introduced implement is projected is formed longitudinally of the flexible tube in side-by-side relationship with the viewing window.
Figure 3:
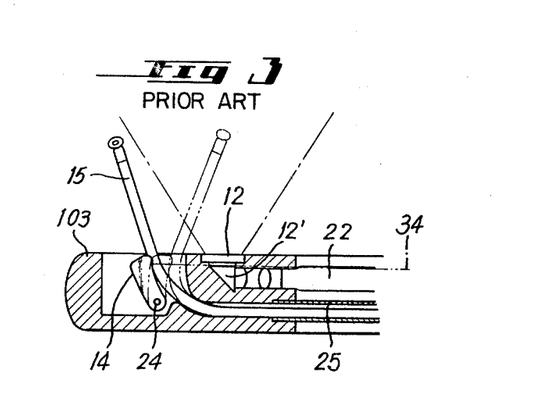
FIG. 3 is a longitudinal section taking along line III—III in FIG. 2.
Figure 4A:
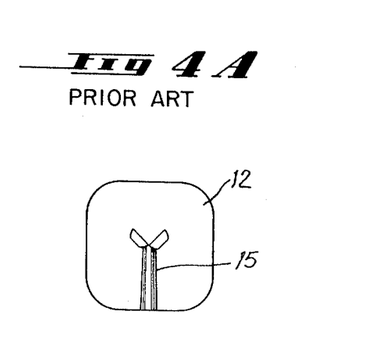
FIG. 4A is a schematic illustration of the visual field of the viewing window in the endoscope for vital tissue inspection wherein the front end metal fitting in which the opening through which the introduced implement is projected is formed longitudinally closer to the front end than to the viewing window.

FIGS. 2 and 3 show an example of a conventional endoscope for vital tissue inspection, in which the front end of the optical fibre bundle for illumination is guided to the front end metal fitting 103 and a light beam transmitted by this optical fibre bundle from the light source is emitted through an illuminating window 13 onto the diseased spot to be inspected. Laterally of said illuminating window 13, there is provided a viewing window 12 having its visual field illuminated by the light beam emitted from said illuminating window 13. More closely adjacent to the front end than to said viewing window 12, opening 14' is formed longitudinally in alignment with said viewing window 12 in the metal fitting 103 through which the front end of the implement 15, described in greater detail below, which has been introduced into tube 102 is projected out from the flexible tube. Within said opening 14', a raiser member 14 is pivotally supported around an axis 24 transversely extending with respect to the depth of said opening 14'. A chain line 34 represents a wire extending from the manipulator unit 101 through the flexible tube 102, and into and through the front end metal fitting 103 and is connected to the upper portion of the raiser member 14 to manipulate said raiser member so that a implement 15 extending through the channel 25 and the opening 14' may be abruptly raised as shown by a chain line 15' by pulling said wire 34 towards the manipulator unit 101 so as to introduce the front end of said implement into the visual field of the viewing window 12 represented by the diverging dot-dash lines. FIG. 4A shows the front end of the implement 15 thus introduced into said visual field. Now, the image of the implement 15 is reversed by a prism 12' arranged just below the viewing window 12, focussed by a lens arranged immediately behind said prism 12' and then transmitted by the optical fibre bundle 22 for observation to said viewer unit 108. In the illustrated example of the prior art, the front end of the implement 15 which is projected outwardly from the flexible tube is raised and laid down in an axially extending plane and including the optical centre axis of a transparent plate covering the viewing window 12, as understood from FIG. 4A, so that the front end of the implement 15 can be easily guided into the visual field of the viewing window 12. However, formation of the opening 14' which must be longitudinally elongate to allow raising and laying down of the front end of the implement as well as the formation of the viewing window 12 longitudinally in the alignment with said opening 14' necessarily results in the front end metal fitting 103 having a relatively large size in longitudinal direction. Insertion of such front end metal fitting 103 into the body cavity inevitably causes pain to the patient and, when it is desired to collected vital tissue from the wall of the duct cavity which is relatively short and narrow, for example, the duodenal cap, the inner wall of such organ prevents the introduced implement 15 from being raised enough to bring the front end of said implement 15 into the visual field of the viewing window 12. This is a critical disadvantage in that not only will vital tissue collection within the narrow duct cavity be obstructed but even the introduction of a pancreatic or bile duct photographing tube into the opening of the target organ will also be obstructed.

Figure 4B:
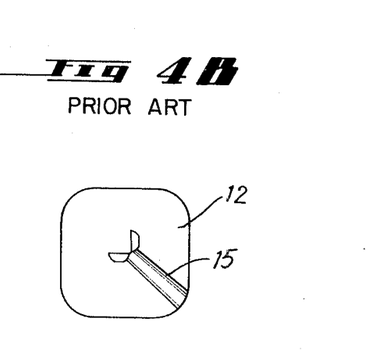
FIG. 4B is a schematic illustration of the visual field of the viewing window in the endoscope for vital tissue inspection wherein the front end metal fitting in which the viewing window is formed laterally in side-by-side relationship with the opening through which the introduced implement is projected.
Figure 5A:
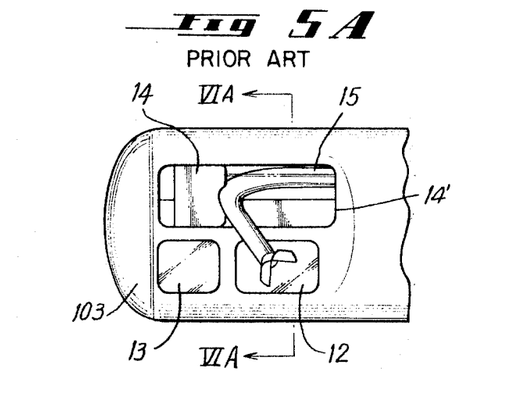
FIG. 5A is an enlarged plan view showing a part of the front end metal fitting arranged at the front end of the flexible tube in an endoscope for vital tissue inspection of the prior art, in which a viewing window is formed laterally in side-by-side relationship with the opening through which the introduced implement is projected while the viewing window and an illuminating window are formed longitudinally in side by side relationship.
Figure 6A:
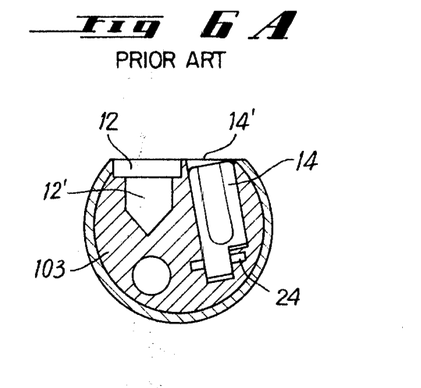
FIG. 6A is an enlarged longitudinal section take along line VIA—VIA in FIG. 5A.

In an attempt to overcome these drawbacks, another endoscope of the prior art for vital tissue inspection as shown by FIG. 5A. FIG. 6A has already been employed in practice. Unlike the embodiment shown in FIGS. 2 and 3, the front end of this improved endoscope is formed with the illuminating window 13 longitudinally in alignment with the viewing window 12 along the length of the flexible tube 102 and with the opening 14', through which the implement 15 which has been introduced into the flexible tube 102 is projected outwardly from the front end metal fitting 103, formed laterally in a side-by-side relationship with said viewing window 12. In this manner, even when it is desired to inspect a diseased spot on the inner wall of a duct cavity which is narrow and short in the direction in which the front end metal fitting 103 is inserted, the inner wall of such duct cavity will not prevent the front end of the implement 15 from being raised and laid down, since said front end of the implement 15 is initially located just laterally of the viewing window 12. However, the front end of the implement 15 must be raised upwardly with a twist so oriented that said front end of the implement is brought close to the central axis of the viewing window 12, since said front end of the implement would tend to be out of the visual field of the viewing window 12 if said front end is raised and laid down in a plane extending in parallel to the plane including the central axis of said visual field. To resolve this problem, the raiser member 14 is pivotally supported around the tilted transverse axis 24, as seen in FIG. 6A, and thereby the plane in which the front end of the implement 15 is raised and laid down is tilted at a certain angle with respect to the plane including the central axis of said visual field. In this manner, the implement 15 is introduced through the inlet opening 109 into the flexible tube to the opening 14', wherein the front end thereof bears against the raiser member 14 and creeps up along a slope thereof. Now, the front end of the implement 15 is curved and guided into the visual field of the viewing window 12 as said wire 34 is pulled towards the manipulator unit 101 and thereby the raiser 14 is rotated. FIG. 4B schematically illustrates how the visual field of the viewing window 12 appears when the front end of the implement 15 has been thus brought by said manipulation into said visual field. This improved arrangement of the prior art also is still disadvantageous in that the channel 25 through which the implement 15 is introduced into the flexible tube should necessarily have its inner diameter further limited by the tilted arrangement of the raiser member 14. This tilted arrangement of the raiser member 14 restricts the level of the channel 25 within the flexible tube, i.e., said channel 25 could not be lowered to the optimal position, and, in consequence, the implement 15 must be raised upwardly by a relatively short raiser member 14. This means that the force required to pull the raiser member manipulating wire 34 must be higher and a desired smooth manipulation is impossible. Further, a space problem exists in that the arrangement of the raiser 14 and its associated members occupies a relatively large space in the front end metal fitting 103, and this makes it difficult to properly arrange therein the optical fibre bundles, air supply tube and water supply tube which are the required elements in the endoscope.

Figure 5B:
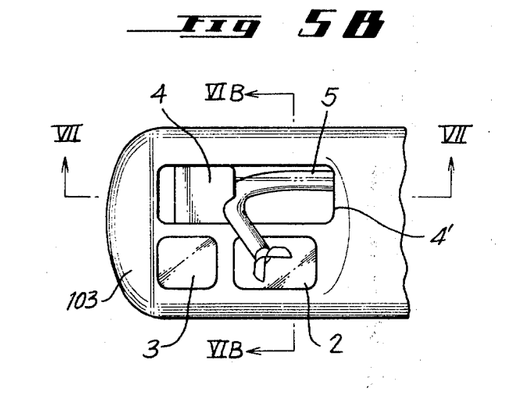
FIG. 5B is an enlarged plan view partially showing the front end metal fitting including the raising means according to the present invention in an endoscope for vital tissue inspection.
Figure 5C:
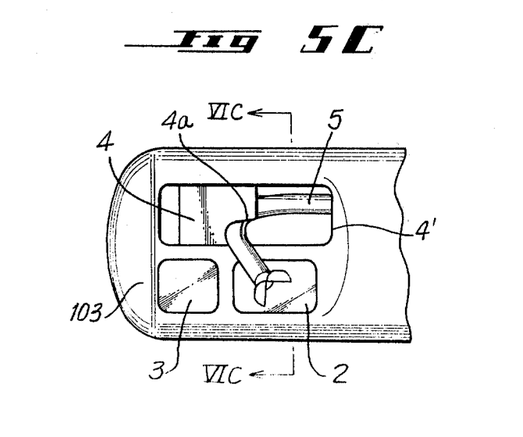
FIG. 5C is an enlarged plan view partially showing the front end metal fitting illustrating another embodiment of the raising means according to the present invention.
Figures 6A, 6B, 6C, 7, 9A, 9B:
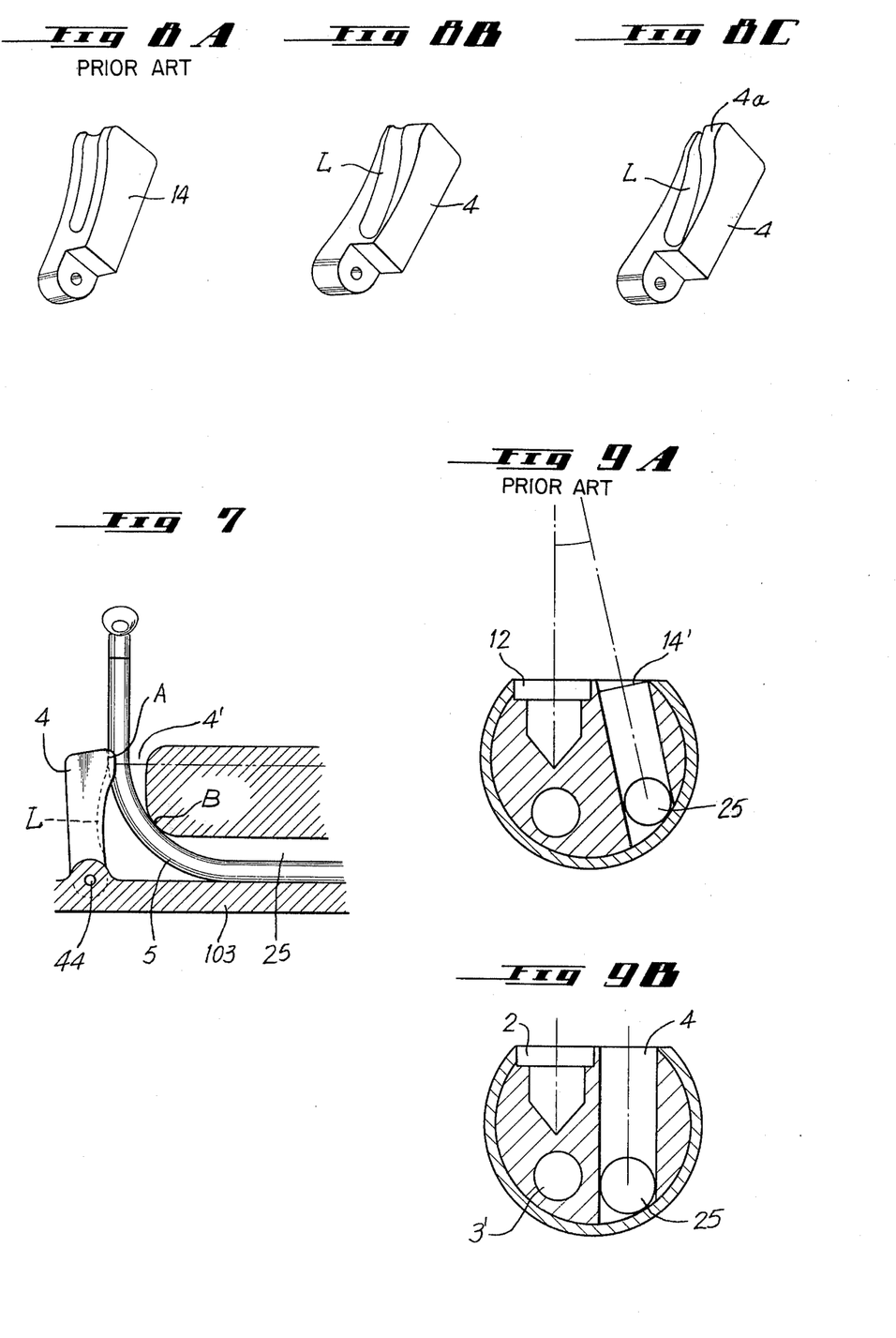
FIG. 6B is an enlarged longitudinal section taken along line VIB—VIB in FIG. 5B.
FIG. 6C is an enlarged longitudinal section taken along line VIC—VIC in FIG. 5C.
FIG. 7 is an enlarged longitudinal section taken along line VII—VII in FIG. 5B.
FIGS. 9A and 9B are transversal, sectional views schematically illustrating the size of the channel through which the implement is introduced and guided, comparing the raising means according to the present invention with the raising means of prior art.
Figure 6B:
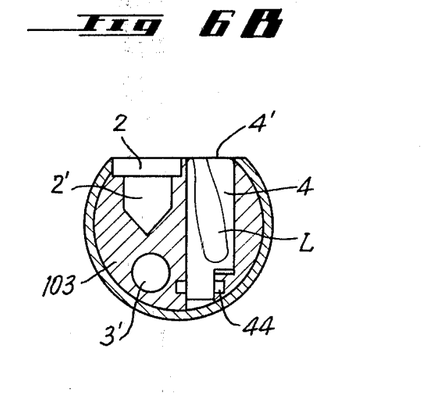
Figure 6C:
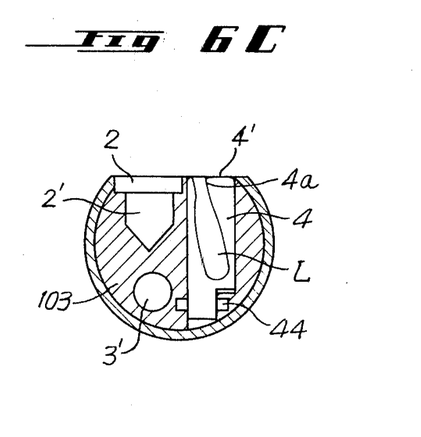
Figure 10:
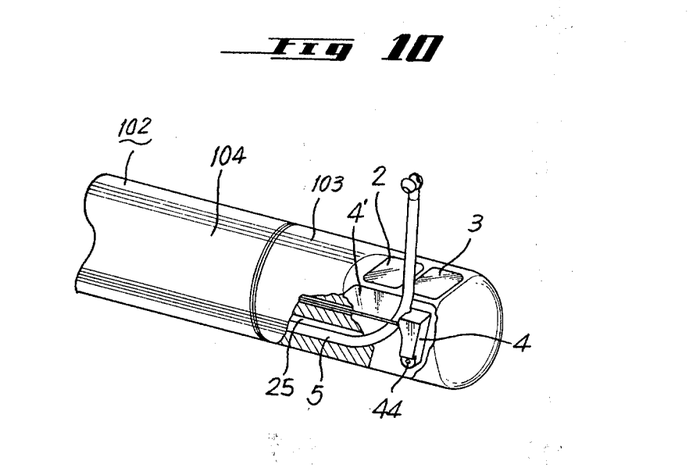
FIG. 10 is a perspective view partially broken away showing the front end of the endoscope for vital tissue inspection including another embodiment of the raising means according to the present invention wherein the raiser member illustrated in FIG. 8C is incorporated within the front end metal fitting.

These drawbacks of the implement raising means of conventional endoscopes are effectively reduced or eliminated by the present invention embodiments of which are illustrated in FIGS. 5B, 5C, 6B, 6C and 10. FIG. 5B and FIG. 6B show an embodiment of the present invention and FIG. 8B shows an embodiment of a raiser member 4 used for this specific embodiment. FIG. 5C and FIG. 6C show another embodiment of the present invention and FIG 8C shows another embodiment of a raiser member 4 used for the second embodiment. Accordingly, one of features of the present invention will be apparent from FIG. 8B and FIG. 8C showing the raiser member 4 used for the present invention and for comparison purposes, FIG. 8A shows the raiser member 14 used for the raising means of the prior art. In these Figures showing the raising means according to the present invention, reference numeral 2 designates the viewing window, 3 designates the illuminating window, 5 designates the implement introduced into the flexible tube, 2' designates a prism arranged just below the viewing window 2 and 3' designates the optical fibre bundle for illumination. Reference numerals in these Figures which are the same as those used in the previous description of the embodiments of prior art respectively designate the same members. The implement raising device according to the present invention is accommodated within an opening 4' formed laterally in side-by-side relationship with the viewing window 2 and, in every embodiment, said opening 4' is formed in parallel relationship to a vertical plane including the optical central axis of the viewing window 2. The raiser member 4 is pivotally supported around a transverse axis 44 extending in parallel to a horizontal plane being orthogonal to said vertical plane adjacent the bottom of said opening 4'. Said raiser member 4 is formed with a slant guide groove L to guide the implement 5 when the latter is raised up and projected out. This groove L is inclined towards the viewing window 2 so that the groove progressively approaches the viewing window 2 as said groove extends from the pivoted end towards the free end of the raiser member 4. The front end of the implement 5 passes through the channel 25, bears against the base of the raiser member 4 at the opening 4' and then creeps up along the guide groove L, as said implement 5 is introduced through the inlet opening 109 into the flexible tube. The front end of the implement 5 thus guided by the slanted guide groove L to be projected towards the viewing window 2 may be further brought with a certain twist into the visual field of the viewing window 2 by pulling the raiser manipulating wire 34 from the manipulator unit 101, although the raiser member 4 is thereby rotated around the horizontal transverse axis 44 in the plane extending in parallel to the vertical plane including the optical central axis of the viewing window 2.

The raising means according to the present invention is similar to the raising device of prior art as shown in FIG. 5A and FIG. 6A, so far as the front end of the implement is guided into the visual field of the viewing window in operative association with the raiser member. However, an important technical significance of the present invention lies in that the raiser 4 is formed with the slanted guide groove L and is pivotally supported by the transverse axis 44 which is not tilted as in one of the improved raising means of the prior art but which horizontally extends perpendicular to the vertical plane including the optical central axis of the viewing window 2 so that the raiser member 4 is rotated in the plane extending in parallel to the vertical plane including the optical central axis of the viewing window 2. It will be apparent from a comparison of FIG. 9A showing the relative position of the viewing window 12 and the raiser member in the raising means of the prior art with FIG. 9B showing the relative position of these members in the raising means according to the present invention that, with the raising means of the prior art in which the pivot axis of the raiser member is tilted and thereby the rotational plane of the raiser itself is also tilted towards the vertical plane including the optical central axis of the viewing window, the width of the raiser member must be reduced under a dimensional restriction imposed on the top cross-section of the opening 14' and the inner diameter of the channel 25 through which the implement should pass must be correspondingly reduced. Obviously, the larger the tilt angle at which of the raiser member is tilted, the smaller the inner diameter of the channel 25 can be and simultaneously the higher or the nearer to the top of the opening 14' the central level of the channel 25 is. As the result, a distance from the pivoted point to a axis of the raiser member which the latter is pulled via the raiser manipulating wire 34 when the raiser is rotated is so shortened that the force required to manipulate the raiser member is increased and thereby the manipulation to direct the front end of the implement to the desired spot within the body cavity cannot be smoothly performed. In order that the effective inner diameter of the channel 25 may be maintained relatively large, and that the projection and orientation of the implement towards the desired spot and collection of vital tissue may be thereby facilitated and injection of contrast medium into pancreatic or bile duct may be effectively performed, it is essential to introduce a tube having an inner diameter which is as large as possible through the channel 25 and to locate the open end of the latter at a position as low as possible. The present invention permits the effective inner diameter of the channel 25 to be maintained adequately large and the channel 25 to be located at a lower level so that it is also possible to obtain the adequate distance from the pivot axis to the point on which the raiser manipulating wire 34 is connected to the raiser member, because the raiser itself is arranged to be rotated in the plane extending in parallel to the vertical plane including the optical central axis of the viewing window according to the present invention. Use of the longer raiser member results in that the projection as well as the orientation of the implement by pulling the raiser manipulating wire 34 can be smoothly performed with a high maneuverability.

Owing to the above-mentioned characteristic that the channel 25 along which the implement 5 is introduced can have a large effective inner diameter, this channel 25 can serve also to remove secretion from the body cavity and mucus which would otherwise stain the viewing window 2, and therefore, it is always possible to keep the visual field clear for easy observation.

The feature of the present invention as mentioned just above is advantageous also to enlarge the angle at which the implement is projected out from the flexible tube. As seen from FIG. 7, the raiser member 4 pulled via the wire 34 urges at a point A on its upper edge against the implement 5 which is, in turn, urged against the front end metal fitting 103 at a point B on the open end of the channel 25. It is desired, therefore, to provide said point B serving as a fulcrum for flexion of the implement's front end adjacent the transverse axis 44 as close as possible while providing the point A upon which the pulling force is exerted as far from the transverse axis 44 as possible in order that the front end of the implement 5 may be effectively curved. However, the rigidity of the implement itself prevents the latter from being sharply bent and, therefore, use of the relatively long raiser member 4 is advantageous in that the front end of the implement 5 is smoothly curved at a relatively large angle under action of a large moment arm. On the other hand, repeated flexion of the implement 5 on the point B serving as the fulcrum certainly tends to cause damage of the implement 5. However, even when not only the peripheral edge defining the open end of the channel 25 is gently rounded as shown by FIG. 7 but also the fulcrum B is slightly spaced from the transverse axis 44 to avoid said damage of the implement 5, such damage or permanent deformation can be avoided without a substantial loss of the desired curving effect and the of angular orientation range of the implement's front end can be maintained relatively wide, since the raiser member 4 is adequately long and the forced exerted point A is sufficiently remote from the pivotal axis in accordance with the present invention.

Figure 11:
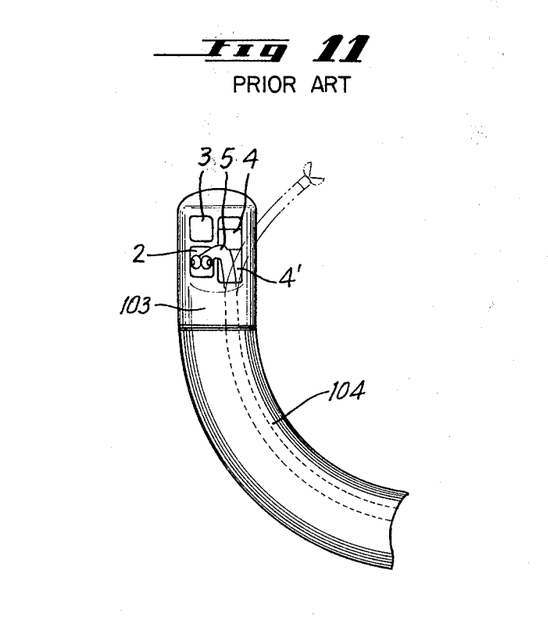
FIG. 11 is a plan view of the front end of the flexible tube of the endoscope illustrating how the front end of the introduced implement is flexibly curved in accordance with the curving habit of the flexible tube's front end.

FIG. 5C, FIG. 6C and FIG. 8C show another embodiment of the present invention. An important feature of this embodiment lies in that said slanted guide groove L is provided on one end or the outer end with a projecting wall 4a. Such arrangement is advantageous in that the front end of the implement projected out from the front end metal fitting 103 is further reliably prevented from being situated out of the visual field of the viewing window particularly when an implement of higher rigidity is handled. Particularly when said wire provided with the forceps or the tube through which the contrast medium is injected into pancreatic or bile duct for observation or photographing purpose has in itself a remarkable flexion habit, said projecting wall 4a is effective in preventing the implement 5 from being projected out of the visual field of the viewing window. In the case where the direction in which the bending portion 104 is curved is in accord with the flexion habit of the implement 5, the front end of the latter is projected in accordance with the direction in which said bending portion 104 is curved. Particularly when the bending portion 104 is curved in the direction away from the viewing window 2 as seen in FIG. 11, the front end of the implement 5 tends to be projected also in the direction away from the viewing window 2. Due to such tendency, the implement 5 tends to be disengaged from the slant guide groove L and to be projected in the direction as indicated by a chain line in FIG. 11, in spite of a sufficient depth of said groove L. In consequence, the front end of the implement cannot be reoriented to the desired spot even when the raiser member 4 is manipulated and the manipulation for introduction of the implement 5 must be inconveniently repeated. With this embodiment illustrated in FIG. 8C, the front end of the implement 5 creeping up along the slant guide groove L is prevented by the projecting wall 4a from being disengaged from said groove L and can be reliably guided by manipulating the raiser member 4 into the visual field of the viewing window 2 even when the implement 5 introduced from the inlet opening 109 has a certain flexion habit and a potential force is exerted on the front end thereof so as to project it out of the visual field of the viewing window due to the correspondence of said flexion habit with the direction in which the bending portion 104 is curved.

What is claimed is:

1. In an endoscope including a manipulator unit having an inlet opening formed therein;

a flexible tube connected with and following said manipulator unit;

a front end metal fitting mounted on a front end of said flexible tube;

a channel provided in said flexible tube communicating with said opening formed in said manipulator unit and through which a desired implement, inserted into said inlet opening, can be guided through said flexible tube to said front end metal fitting;

a first optical fibre bundle for illumination extending through said manipulator unit and said flexible tube to an illuminating window formed in said front end metal fitting;

a second optical fibre bundle for observation extending from a viewer unit provided on said manipulator unit through said flexible tube to a viewing window formed in said front end metal fitting;

an opening formed in the front end metal fitting laterally of said viewing window and communicating with said channel;

a raiser member located in side-by-side relationship with said viewing window and pivotally supported within said opening; and a raiser manipulating wire extending from a free end of said raiser member through said front end metal fitting and said flexible tube to said manipulator unit so that said raiser member may be rotated by pulling the wire from the exterior of said manipulator unit;

wherein the front end of said implement introduced through said inlet opening formed in said manipulator unit into the flexible tube is guided by a guiding effect and a pivotal movement of said raiser into a visual field of the viewing window, the improvement comprising:

raising means characterized by that said raiser member is pivotally supported by a transverse axis extending substantially orthogonally with respect to a vertical plane including the optical central axis of said viewing window and said raiser member further includes a slanted guide groove in the surface thereof in opposed relationship to the open end of said channel, said slanted guide groove being inclined towards said viewing window, wherein said raiser manipulating wire is pulled from the exterior of said manipulator unit and thereby said raiser member is rotated around said transverse axis in a plane substantially parallel to the vertical plane including the optical central axis of said viewing window so that the front end of the implement which creeps up along said slanted guide groove and has been projected outwardly from said front end metal fitting may be guided into the visual field of the view window.

2. The combination according to claim 1 characterized by that said slanted guide groove of said raiser member is provided with a projecting wall along the side edge of said groove on the side thereof distant from the viewing window.

3. In an endoscope including an elongated flexible tube, a manipulator unit associated with one end of said flexible tube, a fitting associated with the other end of said flexible tube, a viewing window formed in said fitting, an opening formed in said fitting in transverse side-by-side relationship to said viewing window and channel means formed in said flexible tube extending between said manipulator unit and said opening formed in said fitting through which an elongated implement can be guided from the manipulator unit to said opening, the improvement comprising:

a raiser member mounted in said opening for pivotal movement in a plane substantially parallel to the vertical plane which includes the optical central axis of the viewing window, said pivotal movement being with respect to a transverse axis extending substantially orghogonally with respect to said vertical plane, and wherein a guide groove is formed in said raiser member in opposed relationship to one end of said channel means, said guide groove slantingly extending at an angle upwardly towards said viewing window.

4. The combination of claim 3, wherein said raiser member includes a wall portion projecting therefrom formed on a side of the guide groove distant from the viewing window.

* * * * *